United States Patent
Buchalova et al.

(10) Patent No.: US 11,730,685 B2
(45) Date of Patent: Aug. 22, 2023

(54) SKIN COMPOSITION BOOSTER OIL

(71) Applicant: Conopco, Inc., Englewood Cliffs, NJ (US)

(72) Inventors: Maria Buchalova, Sandy Hook, CT (US); Teanoosh Moaddel, Watertown, CT (US)

(*) Notice: Subject to any disclaimer, the term of this patent is extended or adjusted under 35 U.S.C. 154(b) by 0 days.

(21) Appl. No.: 16/629,812

(22) PCT Filed: Jun. 21, 2018

(86) PCT No.: PCT/EP2018/066641
§ 371 (c)(1),
(2) Date: Jan. 9, 2020

(87) PCT Pub. No.: WO2019/011619
PCT Pub. Date: Jan. 17, 2019

(65) Prior Publication Data
US 2021/0000712 A1    Jan. 7, 2021

(30) Foreign Application Priority Data
Jul. 12, 2017  (EP) .................................. 17180847

(51) Int. Cl.
*A61K 8/31* (2006.01)
*A61K 8/67* (2006.01)
*A61K 8/37* (2006.01)
*A61Q 19/00* (2006.01)
*A61Q 19/08* (2006.01)
*A61K 8/34* (2006.01)
*A61K 8/89* (2006.01)

(52) U.S. Cl.
CPC ............... *A61K 8/31* (2013.01); *A61K 8/347* (2013.01); *A61K 8/375* (2013.01); *A61K 8/671* (2013.01); *A61K 8/89* (2013.01); *A61Q 19/007* (2013.01); *A61Q 19/08* (2013.01); *A61K 2800/52* (2013.01); *A61K 2800/882* (2013.01)

(58) Field of Classification Search
CPC ...... A61Q 19/00; A61Q 19/08; A61Q 19/007; A61K 8/347; A61K 2800/31; A61K 8/31; A61K 8/585; A61K 2800/52; A61K 8/671; A61K 8/89; A61K 8/375; A61K 8/37; A61K 2800/882; A61K 8/37
See application file for complete search history.

(56) References Cited

U.S. PATENT DOCUMENTS

| | | | |
|---|---|---|---|
| 4,438,095 A | 3/1984 | Grollier et al. | |
| 6,093,411 A * | 7/2000 | Bissett | |
| 6,117,436 A | 12/2000 | Flemming et al. | |
| 7,959,913 B2 | 6/2011 | Granger et al. | |
| 8,124,063 B2 | 2/2012 | Harichian et al. | |
| 8,226,933 B2 | 7/2012 | Granger et al. | |
| 8,409,550 B2 | 2/2013 | Granger et al. | |
| 8,642,665 B2 | 4/2014 | Craig et al. | |
| 8,877,820 B2* | 11/2014 | Oddos ................... | A61K 31/277 514/730 |
| 2007/0025938 A1 | 2/2007 | Hansenne et al. | |
| 2007/0025947 A1 | 2/2007 | Hansenne et al. | |
| 2009/0017078 A1* | 1/2009 | Buderer ................... | A61K 8/26 424/400 |
| 2012/0121737 A1* | 5/2012 | Vielhaber ................ | A61P 17/00 424/737 |
| 2016/0000669 A1 | 1/2016 | Hinman et al. | |
| 2016/0058775 A1* | 3/2016 | Prasad et al. | |
| 2017/0071834 A1 | 3/2017 | Murugesan et al. | |

FOREIGN PATENT DOCUMENTS

| | | | |
|---|---|---|---|
| DE | 102007021482 | 11/2008 | |
| DE | 102011010158 | 8/2012 | |
| FR | 2645740 | 10/1990 | |
| FR | 2890860 | 3/2007 | |
| FR | 2925298 | 6/2009 | |
| JP | 6179614 | 6/1994 | |
| WO | WO8606275 | 11/1986 | |
| WO | WO2004103302 | 12/2004 | |
| WO | WO2008086724 | 7/2008 | |
| WO | WO2010097564 | 9/2010 | |
| WO | WO2010123865 | 10/2010 | |
| WO | WO2012122678 | 9/2012 | |
| WO | WO2014101743 | 7/2014 | |
| WO | WO2014121733 | 8/2014 | |
| WO | WO2014206137 | 12/2014 | |
| WO | WO2015032319 | 3/2015 | |
| WO | WO-2015059001 A1 * | 4/2015 | ............. A61K 8/347 |
| WO | WO2015074587 | 5/2015 | |
| WO | WO2016206770 | 12/2016 | |
| WO | WO2017173291 | 5/2017 | |

OTHER PUBLICATIONS

Tone Correcting Face Oil; Mintel GNPD; 2014; pp. 1-3; XP002774729.
Search Report and Written Opinion in EP17180847; dated Nov. 3, 2017.
M. Alpbaz et al.; The Measurement of Interfacial Tension By Drop-Weight Method; Commun. Fac. Sci. Univ. Ank. Serie B; 1988; pp. 103-112; vol. 34.
Search Report and Written Opinion in PCTEP2018066641; dated Sep. 10, 2018.

* cited by examiner

*Primary Examiner* — Jianfeng Song
(74) *Attorney, Agent, or Firm* — Edward A. Squillante, Jr.

(57) ABSTRACT

Booster oils with stable oil soluble actives are described. The oils are suitable to be combined with end use compositions in order to enhance the compositions efficacy and ensure superior topical benefits to consumers after application.

5 Claims, No Drawings

SKIN COMPOSITION BOOSTER OIL

FIELD OF THE INVENTION

The present invention is directed to a skin composition booster oil and a cosmetic composition having enhanced efficacy as a result of being boosted with such oil. The booster oil comprises active solubilized therein and may be added to a cosmetic composition via a dosing regimen. The regimen allows for the control of active strength in the composition topically applied to a consumer.

BACKGROUND OF THE INVENTION

Dry skin, age spots, as well as wrinkles are just a few of the imperfections that impact a consumer's skin. Personal care products, including creams and lotions, are typically formulated with actives to address such imperfections. Traditional products typically display shortcomings since actives formulated in the products tend to be unstable and/or interact with each other to yield by-products with little to no known skin benefits. It is also true that active instability and interaction often results in a cosmetic composition that can be discoloured, have malodour or both wherein such characteristics would invariably cause a consumer not to continue to use the product at issue.

There is increasing interest to develop cosmetic compositions that have stable actives and that are able to provide superior efficacy to consumers when they are topically applied.

This invention, therefore, is directed to a skin composition booster oil. The skin composition booster oil has active solubilized therein and is suitable to be added to a cosmetic composition via a dosing regimen to unexpectedly result in cosmetic composition with superior active efficacy when topically applied.

Additional Information

Efforts have been made for developing topical compositions. In U.S. Pat. No. 8,124,063, a composition for moisturizing human skin is described.

Other efforts have been disclosed for making topical compositions that benefit skin. In U.S. Pat. Nos. 8,409,550; 8,226,933 and 7,959,913, compositions containing boosters are described.

Still other efforts have been disclosed for preparing skin benefit compositions. In U.S. Pat. No. 8,642,665, environmentally friendly and low whitening topical compositions are described.

None of the additional information describes a composition as set forth in the present invention as claimed.

SUMMARY OF THE INVENTION

In a first aspect, the present invention is directed to a booster oil comprising:
(a) oil, the oil having a peroxide value from 0 to 4 meq/kg and a polarity index from 20 to 80 mN/m;
(b) oil soluble active
wherein oil makes up from 88 to 99.5% by weight of the booster oil, the booster oil optionally comprising structurant.

In a second aspect, the invention is directed to a cosmetic composition having added thereto the booster oil of the first aspect of the invention.

In a third aspect, the invention is directed to a regimen or method for adding the booster oil of the first aspect of the invention to a cosmetic composition.

All other aspects of the invention will more readily become apparent from the description and examples which follow.

Skin, as used herein, is meant to include skin on the arms, face, feet, neck, chest, hands, legs, buttocks and scalp (including hair). End use composition (water or oil continuous but preferably oil continuous) is a composition for topical application and includes a cream, lotion, balm, serum, gel, mousse, deodorant, antiperspirant, shampoo, conditioner, and liquid personal wash. Active means an ingredient that improves a skin characteristic. The booster oil of the present invention is a composition with oil comprising stable and soluble active that may be combined with the end use composition. Polarity index means the value measured of the interfacial tension of an oil taken against water and measured via the drop weight method (M. Alpbaz et al,: The Measurement of Interfacial Tension by Drop Weight Method, Commun. Fac. Sci. Univ. Ank. Serie B, V 34, p 103, 1988). Peroxide value is a normal oxidation index of an oil as measured by standard iodometric titration. Actives not compatible means when present, their combined benefit can be inferior to the benefit each provides alone. Retinoic acid precursor is defined to mean a component that, when oxidized, can convert to retinoic acid.

Unless explicitly stated otherwise, all ranges described herein are meant to include all ranges subsumed therein. The term comprising is meant to encompass the terms consisting essentially of and consisting of. For the avoidance of doubt, a composition comprising the oil, structurant and active of this invention is meant to include a composition consisting essentially of the same and a composition consisting of the same. Stable, as used to characterize active in the booster oil, means active that remains intact prior to being combined with end use composition. All percentages used herein are meant to be by weight unless stated otherwise. Except in the operating comparative examples, or where otherwise explicitly indicated, all numbers in this description indicating amounts or ratios of materials or conditions and/or physical properties of materials and/or use are to be understood as modified by the word "about".

DETAILED DESCRIPTION OF THE INVENTION

The only limitation with respect to the active that may be used in the booster oil of this invention is that the same is soluble therein and provides a benefit to skin when topically applied.

Illustrative examples of the actives suitable for use in this invention include those which are oil soluble like Vitamin A, D, E and K (and their oil soluble derivatives), sunscreens like ethylhexylmethoxycinnamate, bis-ethyl hexyloxyphenol methoxyphenol triazine, 2-ethylhexyl-2-cyano-3,3-diphenyl-2-propanoic acid, drometrizole trisiloxane, 3,3,5-trimethyl cyclohexyl 2-hydroxybenzoate, 2-ethylhexyl-2-hydroxybenzoate or mixtures thereof.

Additional oil soluble actives suitable for use include resorcinols like 4-ethyl resorcinol, 4-hexyl resorcinol, 4-phenylethyl resorcinol, 4-cyclopentyl resorcinol, 4-cyclohexyl resorcinol, 4-isopropyl resorcinol or mixture thereof. Also, 5-substituted resorcinols like 4-cyclohexyl-5-methylbenzene-1,3-diol, 4-isopropyl-5-methylbenzene-1,3-diol, mixtures thereof or the like may be used. The 5-substituted resorcinols, and their synthesis are described in commonly assigned U.S. Published Patent Application No. 2016/0000669A1.

Even other oil soluble actives suitable for use include omega-3 fatty acids, omega-6 fatty acids, climbazole, farnesol, ursolic acid, myristic acid, geranyl geraniol, oleyl betaine, cocoyl hydroxyethyl imidazoline, hexanoyl sphingosine, 12-hydroxystearic acid, petroselinic acid, conjugated linoleic acid, mixtures thereof or the like.

In an especially preferred embodiment, the oil soluble active used in this invention is a retinoic acid precursor represented by the formula:

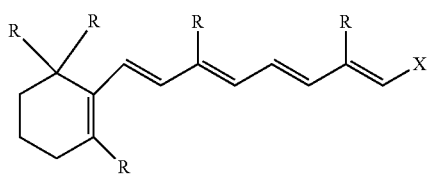

where each R is independently a hydrogen or a $C_{1-6}$ alkyl group and X is

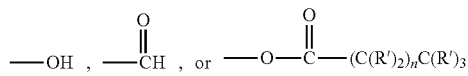

and further where each R' is hydrogen or a $C_1$-$C_3$ alkyl and n is an integer from 0 to 16 (preferably, 1 to 5) and the retinoic acid precursor is retinol, retinal, retinyl propionate, retinyl palmitate, retinyl acetate or a mixture thereof.

Preferably, each R is $CH_3$, each R' is hydrogen and the preferred retinoic acid precursor is retinyl propionate,

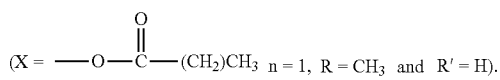

Still another retinoic acid precursor suitable for use is hydroxyanasatil retinoate made commercially available under the name Retextra® as supplied by Molecular Design International. The same may be used in a mixture with the actives described herein.

It is within the scope of this invention for a first and second active to be present in the booster oil of the present invention at a weight ratio of 1.5:0.25 to 0.25:1.5, and typically, at a weight ratio of 1.3:1 to 1:1.3, including all ratios subsumed therein.

In another embodiment, when the booster oil comprises a first active, like a retinoic acid precursor, and a second active not compatible with the first active, like resorcinol, from 2 to 5, and preferably from 3 to 7, and most preferably, from 4 to 10 times more (by weight) of one is used over the other.

In another embodiment, less than 0.3% by weight, and preferably, less than 0.1% by weight, and most preferably, no second active, like resorcinol, is present in the oil when the first active, like a retinoic acid precursor, is present, based on total weight of the booster oil and when the first and second active are not compatible with each other in the same composition.

In still another embodiment, less than 0.3% by weight, and preferably, less than 0.1% by weight, and most preferably, no first active, like a retinoic acid precursor, is present when a second active, like resorcinol, is present, based on total weight of the booster oil and when the first and second active are not compatible with each other in the same composition.

In a preferred embodiment, a retinoic acid precursor and a resorcinol are present in the booster oil at a weight ratio from 0.6:1.0 to 1.0:0.6, and preferably, from 0.8:1 to 1 to 0.8.

Typically, the amount of oil soluble active used in this invention is from 0.001 to 2.5%, and preferably, from 0.01 to 2%, and most preferably, from 0.05 to 2% by weight, based on total weight of booster oil and including all ranges subsumed therein.

In a most preferred embodiment, the booster oil of the present invention has retinyl propionate and hexyl- and/or ethyl resorcinol as active. In another preferred embodiment, the booster oil comprises as active retinyl propionate and climbazole.

Oils (i.e., carrier oil to make booster oil with soluble active) suitable for use in this invention include those having a peroxide value from 0 to 4, and preferably, from 0.0 to 3.5, and most preferably, from 0.0 to 2.25. Such oils will also have a polarity index from 0.1 to 80 mN/m, and preferably, from 1.0 to 75 mN/m, and most preferably, from 10 to 70 mN/m.

Illustrative examples of oils suitable for use in this invention include hydrocarbons and polymer oils like mineral oil, squalane, squalene, isohexadecane or hydrogenated polyisobutene; and silicone oils like dimethicone (e.g., DC245, made commercially available from Dow Chemical) or cyclomethicone; and esters like isopropyl myristate, isopropyl palmitate, isopropyl isostearate, isostearyl palmitate, isostearyl myristate, isostearyl isostearate, oleyl oleate, decyl oleate, decylcocoate, ethylhexylhydroxystearate, ethylhexyl palmitate, ethylhexyl stearate, cetearyl ethylhexanoate, cetearyl isononanoate, propylene glycol dicaprylate/dicaprate or caprylic capric triglyceride. Mixtures of the above oils may be used, but an often preferred oil is one comprising at least 3%, and preferably, at least 5%, and most preferably, at least 7% to 100% by weight caprylic capric triglyceride, mineral oil, silicone oil and/or ester oil (such as isopropyl palmitate), based on total weight of oil in the booster oil.

Oil typically makes up from 88 to 99.5%, and preferably, from 90 to 96%, and most preferably, from 90 to 94% by weight of the total weight of booster oil, including all ranges subsumed therein. In a preferred embodiment, the booster oil of the present invention consisting essentially of oil and oil soluble active, and more preferably, oil, oil soluble active and structurant, and use of the booster oil to boost end use composition is most desirable.

The end use compositions suitable to be combined (i.e., dosed or used with) the booster oil of the present invention are typically emulsions that comprise from 2 to 98% by weight water. Such emulsions may comprise from 2 to 98% by weight oil whereby the oil may be identical to that of the oil used to make the booster oil with soluble active as defined herein.

The emulsifiers suitable for use in the end use composition that is dosed with booster oil typically have an HLB from 5 to 20, and preferably, from 5 to 18, and most preferably from 5 to 7, including all ranges subsumed therein. Illustrative examples of the types of emulsifiers suitable for use in the end use composition described in this invention include ceteareth-20, cetearyl glucoside, ceteth-10, ceteth-20, isosteareth lauramide, lecithin, linoeamide, oleth-10, PEG-20, methyl glucose sesquistearate, polysorbate 20, polysorbate 40, polysorbate 60, polysorbate 80, polysorbate 85, stearamide MEA, mixtures thereof or the like.

Emulsifiers sold under the names Scatties®, Tween®, Alkest® and Canarcel® are suitable for use. Preferred emulsifiers include those with an HLB of 7 or under such as glyceryl laurate, ceteth 2, glyceryl stearate, PEG-4 dilaurate and the like.

Emulsifiers typically make up from 0.1 to 25%, and preferably, from 0.5 to 20%, and most preferably, from 0.8 to 5% by weight of the end use composition, including all ranges subsumed therein. As noted, the end use composition may be an oil-in-water or water-in-oil composition, but it is preferably a water-in-oil composition. The end use compositions suitable to be combined (i.e., dosed or used with) the booster oil of the present invention can also include double emulsions with the external phase preferably being oil.

Preservatives can desirably be incorporated into the end use composition of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, 1,2-octanediol, hydroxyacetophenone, ethylhexylglycerine, hexylene glycol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight in the end use composition, including all ranges subsumed therein. Combinations of 1,2-octanediol and phenoxyethanol, or iodopropynyl butyl carbamate and phenoxyethanol are often preferred. Also preferred is a preservative system with hydroxyacetophenone alone or in a mixture with other preservatives.

Thickening agents (structurants) may optionally be included (preferably are included) in the booster oil (when they are oil soluble) of the present invention as well as the end use composition being combined with booster oil. Particularly useful are oil soluble thickening agents such as for example ViscUp™ (hydrogenated styrene butadiene copolymer) made commercially available by Lonza. Other suitable thickening agents can include Silicone elastomers, fumed silica, magnesium-aluminum silicate. Still others could include polyamides such as those sold under the tradename Sylvaclear™, Sylvasol™, Uniclear™, Sylvagel™. Clays such as Betonite, hectorite are also suitable oil gellants. Also other suitable gellants can include natural organophilic layered silicates sold under tradename Tixogel™, Garamite™. Still other thickening agents can include hydrogenated castor oil sold under the tradename Rheocin™. Hydrophobically modified polysaccharides can also be used. Examples include hydrophobically modified starches, natural/synthetic gums and cellulosics.

In the case of the water phase of the end use composition, maltodextrin, xanthan gum, citrus fibers and carboxymethyl cellulose are the often preferred thickening agents used. Structurant typically makes up from 0.001 to 20%, and preferably, from 0.1 to 16%, and most preferably, from 0.25 to 12.5% by weight of the booster oil and/or the end use composition, including ranges subsumed therein. In an especially preferred embodiment, structurant is present in the booster oil at a weight percent of 2.5 to 6.5% by weight of the total weight of booster oil, including all ranges subsumed therein.

Fragrances, fixatives and exfoliants may optionally be included in booster oil and/or end use composition of the present invention. Each of these substances may range from about 0.05 to about 5%, preferably between 0.1 and 3% by weight.

Conventional humectants may optionally be employed as additives to the end use composition of the present invention as a skin benefit agent. These are generally polyhydric alcohol type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof.

The amount of humectant employed may range anywhere from 0.0 to 15% by weight of the total weight of the end use composition.

Conventional sensory particles may optionally be employed such as for example polyethylene, polymethylmethacrylate, silica beads sold by KOBO. These typically make up from 0.1 to 2.0% y weight of the end use composition when they are used.

The end use composition of the present invention may optionally include water soluble actives like Vitamin $B_2$, Vitamin $B_3$ (niacinamide), Vitamin $B_6$, Vitamin C and the like. Derivatives of the vitamins may also be employed.

For instance, Vitamin C derivatives such as ascorbyl tetraisopalmitate, magnesium ascorbyl phosphate and ascorbyl glycoside may be used. Other water soluble actives suitable for use in the water continuous phase of the end use composition and extracts like sage, aloe vera, green tea, grapeseed, thyme, chamomile, liquorice or rosemary extract or mixtures thereof. Still other water soluble actives suitable for use include alpha hydroxyacids like lactic and glycolic acid, beta hydroxy acids like salicylic acid, amino acids like cystine, arginine, lysine, glutamine, glycine, glutamic acid (and its derivatives, like pyroglutamic acid), alanine, valine and skin benefit agents like ferulic acid, hyaluronic acid, and allantoin. Water soluble sunscreens like ensulizole may also be used. Total amount of water soluble actives (including mixtures) suitable for use in the end use composition of this invention may range from 0.0 to 15%, preferably from 0.001 to 10%, optimally from 0.01 to 4% by weight based on total weight of the end use composition and including all ranges subsumed therein.

When making the booster oil of the present invention, the desired ingredients may be mixed to produce the oil continuous composition having soluble active therein. Typically moderate shear is used under atmospheric conditions with temperature being from ambient to 85° C. The end use compositions suitable for use in this invention may be mixed via conventional methods including those which use standard homogenization techniques. The end use compositions suitable for use can also be those which are commercially available.

In a preferred embodiment, the booster oil of the invention has a viscosity from 750 to 15,000 cps, and preferably, from 2,000 to 10,000 cps, and most preferably, from 4,000 to 7,000 cps, including all ranges subsumed therein, where the viscosity of the booster oil may be measured with a Brookfield (DV-1+) Viscometer, temperature 25° C. and set at 20 RPM, RV6 for 30 seconds.

The booster oil of the present invention typically should have less than 5% by weight water, and preferably, 0.0 to 2.5% by weight water based on total weight of the booster oil and including all ranges subsumed therein. In a most preferred embodiment, the booster oil is anhydrous, and therefore, free of water.

The oil soluble actives described for use in the booster oil of this invention may also be present within the oil phase of the end use composition. Typically, such oil soluble actives make up from 0.0 to 20%, and preferably, from 0.01 to 16%, and most preferably, from 1.0 to 12% by weight of the end use composition, including all ranges subsumed therein. In an especially preferred embodiment, from 0.001 to 6%, and most preferably, from 0.03 to 3.5% by weight of a resorcinol derivative is present in the oil phase of the end use composition with no retinoic acid precursor present therein.

If gels are desired, to the booster oil may be added oil based gelling agents like those comprising lecithin, phospholipids, phytostearol or mixtures thereof. Such agents typically make up from 0.1 to 2%, and preferably, from 0.5 to 1.5% by weight of the booster oil, including all ranges subsumed therein.

The booster oil of the present invention is dosed into the end use composition and typically a consumer is instructed to combine booster oil with end use composition already in the consumer's hand. The same may first be mixed in a small vessel like a reusable plastic cup. Instructions on how much booster to combine with end use composition will be provided so that the consumer, by mixing in his or her hands (stirring or collectively on his or her body), will produce a well-mixed and enhanced end use composition that has intact active ready to apply to skin in need of an improvement. Typically, instructions will be provided to not use the booster oil alone and only in combination with end use composition. Booster dosing may be achieved with a package suitable to release drops or with a package having an eye dropper, preferably with volume marked. Typically, the consumer will be instructed to use from 2 to 8 and preferably, from 4 to 6 times by weight more end use composition than booster oil, including all ranges subsumed therein.

The end use compositions suitable for boosting with booster oil of this invention are limited only to the extent that they may be topically applied to provide a consumer benefit. Superior products made commercially available by Unilever® under the brand names Dove®, Ponds®, Simple®, Vaseline®, Fair and Lovely®, St Ives®, Noxema®, Suave®, Kate Somerville® and the like are especially preferred for use with the booster oil of this invention.

The Examples provided are to facilitate an understanding of the invention. They are not intended to limit the scope of the claims.

Example 1

The following ingredients were mixed under moderate shear (atmospheric pressure conditions and temperature at 40° C.) to produce booster oils consistent with this invention. Amount of active present was determined by HPLC.

| Ingredient | Weight Percent |
| --- | --- |
| Caprylic Capric Triglyceride (CCT) | Balance |
| Isopropyl Palmitate | 36% |
| Mineral Oil 70 | 47% |
| Silicone Oil (DC245) | 2% |
| 4-Hexyl Resorcinol | 0.4% |
| Retinyl Propionate | 0.37% |
| Climbazole | 0.25% |
| ViscUp ™ (hydrogenated styrene butadiene copolymer) | 4% |

The booster oil made according to this Example when stored at 45° C. for three months surprisingly displayed nearly no visible color change with 90% of the original amount of hexyl resorcinol used and 80% of the original amount of retinyl propionate used remaining intact. The results show that active level and selection of oil consistent with the criteria set out in this invention unexpectedly yield an oil based booster with stable active.

Example 2

The following ingredients were mixed in a manner similar to the one described in Example 1.

| Sample 1 | % by weight | Sample 2 | % by weight | Sample 3 | % by weight | Sample 4 | % by weight |
| --- | --- | --- | --- | --- | --- | --- | --- |
| Caprylic capric triglyceride | 99.2 | Caprylic capric triglyceride | 91 | Caprylic capric triglyceride | 75 | Caprylic capric triglyceride | 50 |
| Retinyl propionate | 0.4 | Retinyl propionate | 4.3 | Retinyl propionate | 12 | Retinyl propionate | 24 |
| 4-hexyl resorcinol | 0.4 | 4-hexyl resorcinol | 4.7 | 4-hexyl resorcinol | 13 | 4-hexyl resorcinol | 26 |

Surprisingly, after storage for 5 days at 45° C. and HPLC analysis, the following results were obtained.

| | % Retinyl Propionate Remaining | % 4-Hexyl Resorcinol Remaining |
| --- | --- | --- |
| Sample 1 | 100 | 93 |
| Sample 2 | 73 | 86 |
| Sample 3 | 7 | 56 |
| Sample 4 | 0 | 49 |

The results indicate that when active exceeds 2.5%, stability of the active is compromised.

Example 3

The following Samples were made by mixing ingredients in a manner similar to the one described in Example 1. The Samples were stored for 11 days at 70° C.

| Ingredient | Sample 5 (wt %) | Sample 6 (wt %) | Sample 7 (wt %) | Sample 8 (wt %) | Sample 9 (wt %) | Sample 10 (wt %) | Sample 11 (wt %) | Sample 12 (wt %) |
|---|---|---|---|---|---|---|---|---|
| Retinyl Propionate | 0.5 | 0.5 | 0.5 | 0.5 | 0.5 | 4.3 | 0.4 | 4.3 |
| 4-Hydroxy Resorcinol | — | 0.4 | — | 0.4 | 0.4 | 4.7 | 0.4 | 4.7 |
| Isopropyl Palmitate | 99.6 | 99.2 | — | — | 99.2 | 91 | — | — |
| Isopropyl Isostearate | — | — | 99.6 | 99.2 | — | — | 99.2 | 91 |

Surprisingly, after storage and assessment with HPLC analysis, the following results were obtained.

|  | % Retinyl Propionate Remaining | % 4-Hexyl Resorcinol Remaining |
|---|---|---|
| Sample 5 | 8 | — |
| Sample 6 | 45 | 100 |
| Sample 7 | 0 | — |
| Sample 8 | 16 | 58 |
| Sample 9 | 45 | 100 |
| Sample 10 | 2 | 46 |
| Sample 11 | 16 | 58 |
| Sample 12 | 9 | 69 |

The results indicate that when oil and/or active amount is/are used in a manner that does not meet the criteria of the present invention, stability of the actives present decreases.

Example 4

Booster oil similar to the one made in Example 1 was combined with a commercially available lotion (Pond's age miracle™) to further enhance the performance of the latter. The panelists were instructed to utilize 5 parts of end use composition for every part of booster oil and to combine the components with shear in a reusable cosmetic cup. The resulting end use product was then applied to the panelist's hands to deliver excellent topical benefits. Surprisingly, the composition was easy to mix and apply. The composition did not result in unpleasant sensory characteristic upon application.

The invention claimed is:

1. A booster oil comprising:
   (a) oil, the oil having a peroxide value from 0 to 4 meq/kg and a polarity index from 20 to 80 mN/m, the oil comprising caprylic capric triglyceride and less than 2.5% by weight water; and
   (b) oil soluble active
   wherein oil makes up from 88 to 99.5% by weight of the booster oil, the booster oil optionally comprising structurant, wherein the oil further comprises silicone oil, mineral oil, isopropyl palmitate or a mixture thereof, wherein a 0.1 to 2% by weight lecithin, phospholipid, phytosterol or a mixture thereof is present in the booster oil wherein the oil soluble active is present in an amount from 0.001 to 2.5%, based on total weight of booster oil, and further wherein the oil soluble active consists essentially of retinyl propionate and 4-hexyl resorcinol at a weight ratio of 0.6:1 to 1:0.6.

2. The booster oil according to claim 1 wherein the structurant is present at an amount from 2.5 to 6.5 percent by weight.

3. The booster oil according to claim 1 wherein the booster oil further comprises climbazole.

4. The booster oil according to claim 1 wherein the booster oil is suitable to boost efficacy of an end use composition used to treat a skin condition.

5. The booster oil according to claim 4 wherein the end use composition is a lotion, serum, cream, wash, deodorant, antiperspirant, shampoo or conditioner.

* * * * *